United States Patent
Lewis et al.

[11] 3,937,060
[45] Feb. 10, 1976

[54] MUD GAS CONTENT SAMPLING DEVICE

[75] Inventors: George E. Lewis, Arcadia; Charles P. Peterman, South Laguna, both of Calif.

[73] Assignee: Hydril Company, Los Angeles, Calif.

[22] Filed: Feb. 6, 1974

[21] Appl. No.: 439,892

[52] U.S. Cl. .................................. 73/19; 73/153
[51] Int. Cl.² .................. G01N 7/14; E21B 47/00
[58] Field of Search ............................... 73/19, 153

[56] References Cited
UNITED STATES PATENTS

| | | |
|---|---|---|
| 2,138,141 | 11/1938 | Cromer et al. ............................ 73/19 |
| 2,280,075 | 4/1942 | Hayward ................................ 73/19 |
| 3,521,478 | 7/1970 | Magorien .............................. 73/19 |
| 3,731,530 | 5/1973 | Tanguy et al. ......................... 73/153 |
| 3,802,260 | 4/1974 | Kishel ................................... 73/153 |
| 3,813,935 | 6/1974 | Tanguy et al. ......................... 73/153 |

Primary Examiner—Richard C. Queisser
Assistant Examiner—Frederick Shoon
Attorney, Agent, or Firm—William W. Haefliger

[57] ABSTRACT

The gas content of well drilling mud under pressure is determined by extracting or isolating a sample of the pressurized mud, as for example at a down-hole location, reducing the pressure of the sample, and sensing the fluid pressure of the sample prior to and following such pressure reduction.

14 Claims, 3 Drawing Figures

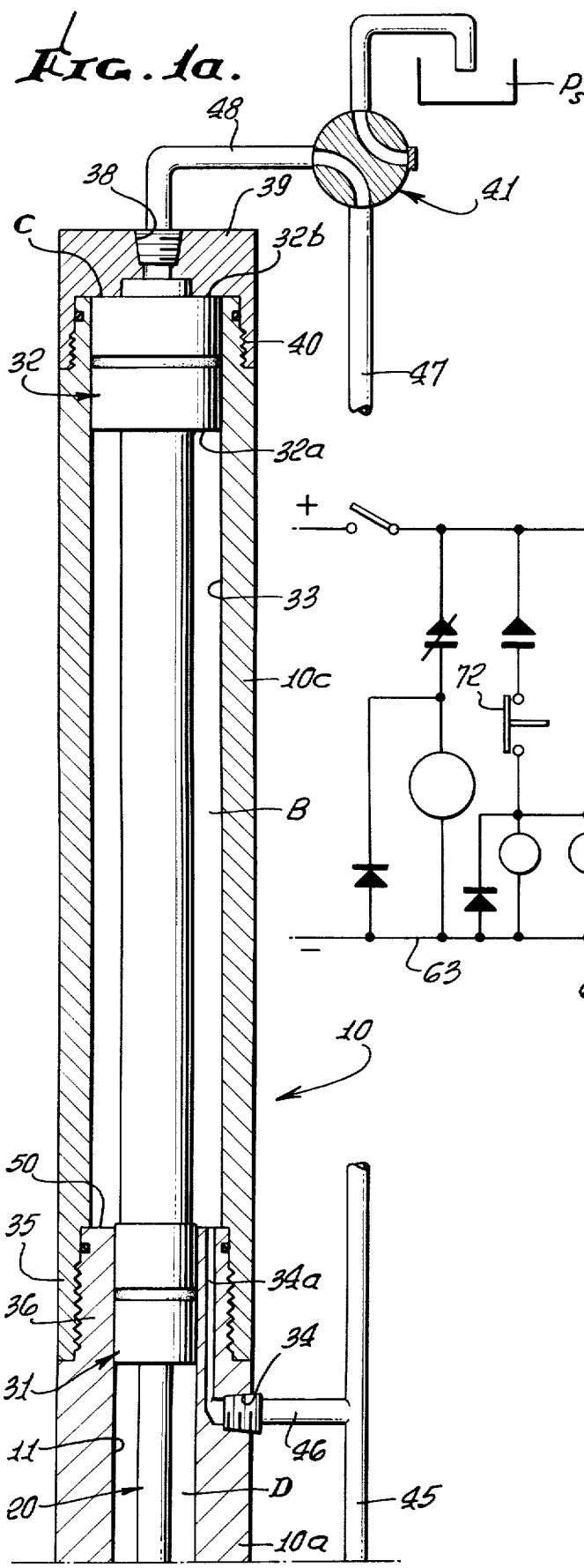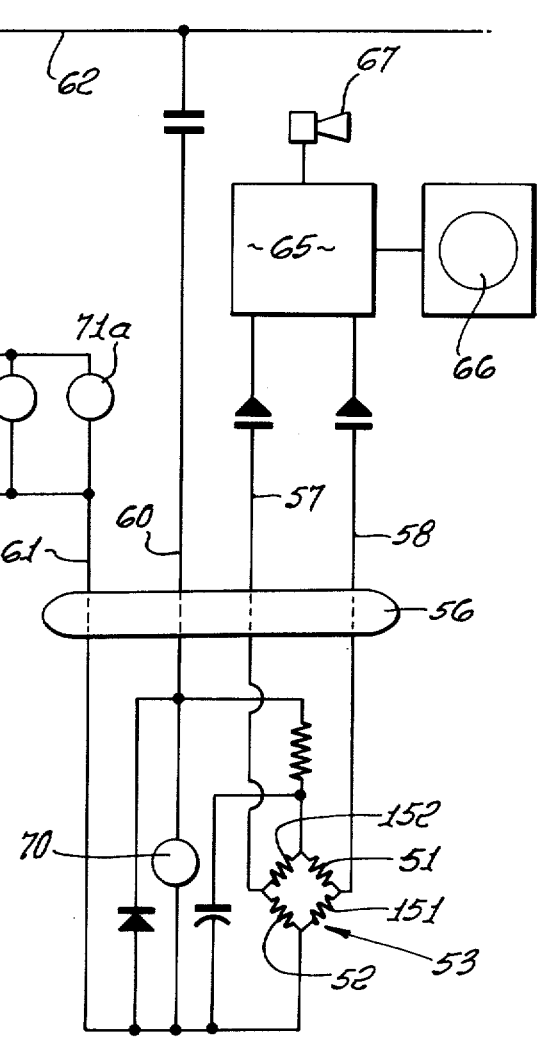

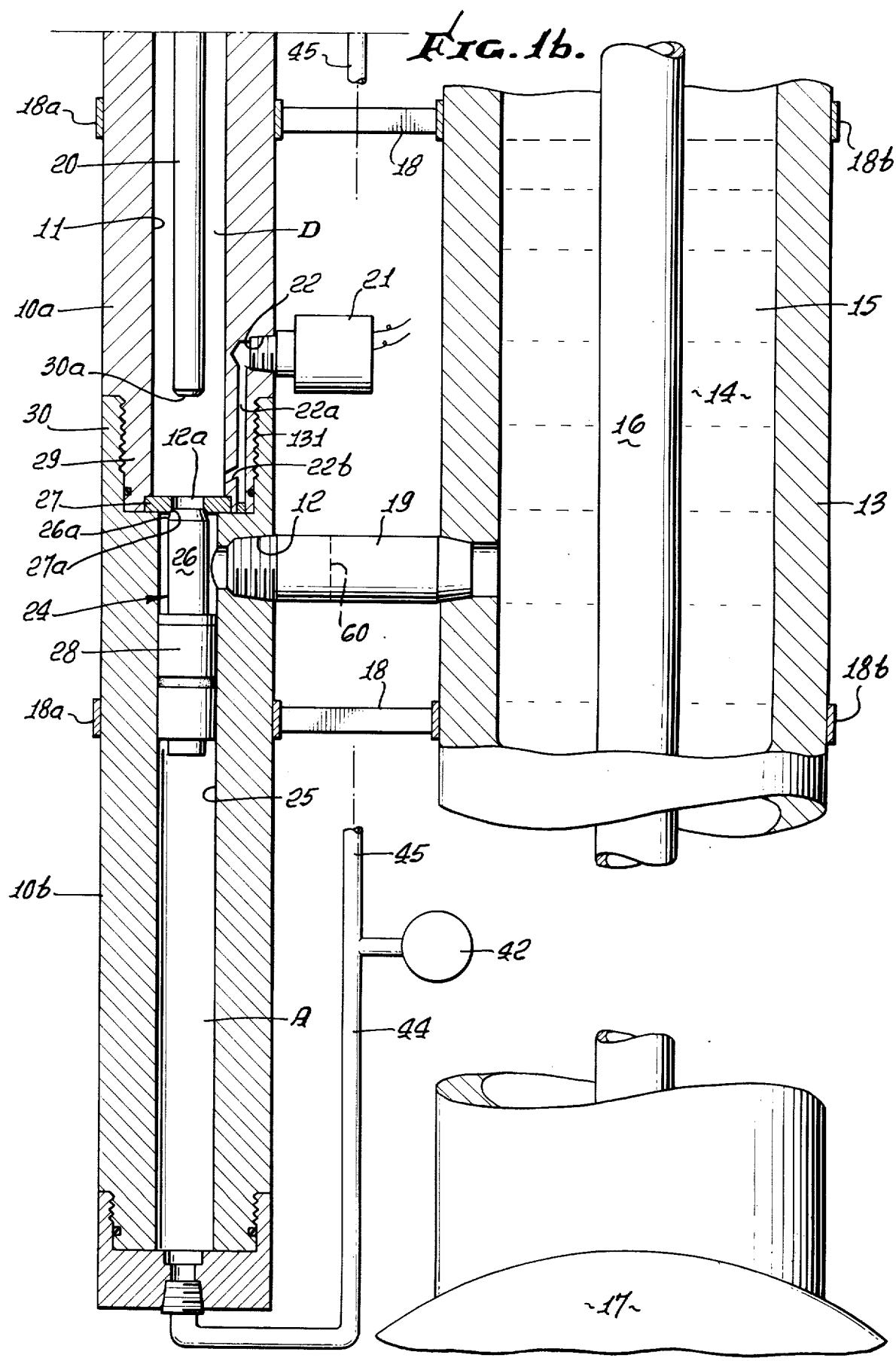

3,937,060

MUD GAS CONTENT SAMPLING DEVICE

BACKGROUND OF THE INVENTION

This invention relates generally to the determination of gas in well drilling mud, before the circulating mud reaches the surface drilling site; more particularly the invention concerns the provision of method and apparatus to determine the gas content of a mud sample through pressure sensing before and after the volume of the sample is increased.

For some time, when drilling subsea, there has been a need for an early warning system to determine the presence of gas in the mud before it reaches the surface, the purpose being to warn the drilling crew of the presence of gas in the mud while it is in the vicinity of the wellhead, rather than wait until that mud has reached the surface. Such a warning would give the crew considerable extra time to secure the well, start to heavy up the mud, and to circulate out any gas cut mud. Unless appropriate steps are taken, the well can blow out, endangering the lives of the crew members, to say nothing of great loss of oil or gas, and damage to the drilling rig.

SUMMARY OF THE INVENTION

It is a major object of the invention to provide a solution to the above described substantial problems. Basically, the invention is embodied in apparatus to extract a sample of the drilling mud from well piping, as for example at an undersea location, to reduce the pressure of the sample, and to sense the pressure of the sample fluid before and after pressure reduction. The two pressures thus sensed may be employed to calculate the gas content of the mud in accordance with a formula to be described.

More specifically, the invention is embodied in a combination that may typically include:

a. a housing defining a mud sample chamber, and having a first bore and a port communicable with well piping containing pressurized mud, b. a first plunger movable in the first bore in one direction to return a mud sample in the chamber out said port to said piping, and movable in the opposite direction in the first bore to ingest a pressurized mud sample into such chamber via said port, and c. valve means controlling said port and responsive to plunger movement in said opposite direction to block flow of mud to the sample chamber prior to subsequent completion of said plunger movement in said opposite direction which effects a predetermined volume increase producing a reduction of pressure exerted by the sample in the chamber, the pressure reduction being indicative of the mud gas content, and d. whereby the fluid pressure of the sample in the chamber may be sensed by a sensor in communication with said chamber both prior to and subsequent to said pressure reduction.

Typically, the valve means may include a second plunger movable in a second bore defined by said housing in response to first plunger movement, said first plunger disengaging the second plunger upon closing of said port and prior to said completion of opposite direction movement of the first plunger.

Further, the invention enables a single source of working fluid to service both plungers and associated pistons, in such a manner as to minimize working fluid use.

These and other objects and advantages of the invention, as well as the details of an illustrative embodiment, will be more fully understood from the following description and drawings, in which:

DRAWING DESCRIPTION

FIG. 1 is an elevation taken in section showing one preferred form of the mud gas control detector; and FIG. 2 is a working diagram.

DETAILED DESCRIPTION

In accordance with the invention, the detector comprises a housing, as for example at 10, having a first bore 11 and a side port 12 communicable with well piping 13 such as casing containing drilling mud 14 in annulus 15. Typically, a drill string 16 extends in the casing 13, and in one application the latter comprises a riser pipe extending upwardly in the ocean from a ball joint 17 at the upper end of a sub-sea stack of well head equipment. A cross-over pipe 19 intercommunicates the port 12 with upwardly circulating mud 14 in the annulus 15. Also, the housing 10 may be suitably attached to pipe 13, as indicated at 18, 18a and 18 b.

A first plunger indicated at 20 is provided to be movable in the first bore 11 in one direction, as for example downwardly, to drive a mud sample in sample chamber D out the port 12 and back to the annulus 15 via cross over pipe 19; similarly, the plunger 20 is movable in the opposite direction, as for example upwardly, to ingest a fresh mud sample into chamber D via pipe 19 and port 12. In this regard, sampling valve means is also provided to be responsive to plunger movement for closing a first control port 12a prior to completion of plunger movement in the opposite or upward direction, so that subsequent completion of such movement will effect a reduction of pressure in the sample of mud ingested into chamber D, thereby expanding gas in the sample. As a result, both the initial "high" pressure $P_2$ of the ingested mud sample, and the later "reduced" pressure $P_4$ of the mud and gas sample may be sensed by a sensor 21 in communication with chamber D, as via another side port 22 having extensions 22a and 22b.

Such valve means may, with unusual advantage, include a second plunger, as for example at 24, movable in a second bore or chamber 25 defined by the housing, and in response to first plunger movement. In this regard, the second plunger may include a reduced diameter valve stopper section such as rod 26 the forward end of which is annularly tapered at 26a to engage annular seat 27a on ring 27, and a piston section 28 integral with the stopper section. Ring 27 is retained between pin 29 on housing section 10a, and box 30 on housing section 10b, the pin and box having threaded interfit at 131.

Piston section 28, slidable in bore 25, receives fluid pressure application in chamber A tending to urge the second plunger in the opposite direction (as for example upwardly) for valve stopper closing engagement with the seat 27a. During ingestion of a mud sample into chamber D, both plungers 20 and 24 move from lowermost positions in their respective bores, the valve means being open, and the upper end of the stopper 26 engaging the lower end face 30a of the elongated rod section 30 of plunger 20. The latter is integral with a piston section 31 of plunger 20, which is slidable in bore 11 and defines the upper end of sample chamber D. As the stopper end of 26a engages seat 27a during upward movement of both plungers, effectively closing port 12a to chamber D, the first plunger disengages the second plunger and continues in its upward movement to reduce the pressure in the sample chamber D, as referred to.

Such upward movement of the first plunger 20 may with unusual advantage be facilitated by working fluid pressure application to a primary piston surface 32a on another piston 32 defined by the first plunger. Piston 32 is shown as slidable in a third bore 33 defined by the housing, and which has a larger diameter than bore 11. As a result, working fluid admitted to chamber B between the pistons 31 and 32 and exerted on such pistons produces net upward force exertion on the first plunger 20. Such pressure may be communicated to chamber B via side or primary porting 34 and 34a. Bore 33 is defined by housing section 10c forming internally threaded box 35 receiving externally threaded pin 36 on housing section 10a.

The first plunger 20 may also have a secondary piston surface, as at 32b defined by piston 32, to receive working fluid pressure application tending to urge the first plunger in said one or downward direction. Such pressure may be communicated to chamber C above surface 32b via end or secondary port 38 in the housing end cap 39 threadably attached to housing section 10c at 40. Note that the common working pressure received in both chambers B and C results in net force exertion to move plunger 20 downwardly, as described above, to drive the mud sample from chamber D, whereas if working pressure is applied to chamber B only, that plunger is driven upwardly. To accomplish this, a three-way control valve 41 is provided to connect chamber C with pressure source 42 in one position of the valve, and to connect chamber C with exhaust pressure $P_x$ in the alternate position of the valve. Accordingly, a single pressure source 42 may be employed to supply all chambers A, B and C with common operating pressure, as via pipes 44–48, chamber B having a larger cross sectional area than chamber A, and chamber C a larger area than chamber B.

To review the operation, pressure in chamber A provides a constant force on the sampling valve piston 28 urging stopper end 26a toward the valve seat 27a. Pressure in chamber B provides an upward force on the piston 32 causing it to move upward. When pressure is applied to chamber C, the operating piston 32 will move down, since its area is greater than the sum of the areas of chambers A and B. When operating, control valve 41 will alternately apply and remove the pressure from chamber C causing the piston to oscillate. During the downward stroke, rod 20 will contact the top of the sampling valve stopper 26, and by continued downward movement opens the sampling valve port 12a allowing the sampling piston 31 to force the charge of mud out of chamber D. Downward travel will stop when the chamber B is reduced to zero volume and shoulder 50 contacts the bottom 32a of piston 32. Upward travel will be initiated when control valve 41 is turned to connect chamber C to the exhaust pressure and pressure in chamber A and B provides the required upward force. Such upward travel will ingest a new charge of mud into chamber D. The valve seat 27a being smaller than the sampling valve stopper surface 26a, it is impossible to ingest 100% new mud; but, with careful dimensional control of these parts, and the size of chamber D, close to 90% new mud can be sampled on each stroke. Since each sample will have the same dilution of old mud, and only small changes of mud content will be evident, between successive samples, the reading of gas content can be adjusted as though 100% new mud were sampled.

Before the end of upward travel of the operating piston 32, the sampling valve plunger 24 will close against seat 27a and will be held tightly closed by the force of working pressure in chamber A. The operating plunger 20 will continue to move upward and consequently pull a vacuum in sample chamber D, the amount of such vacuum depending upon the amount of gas in the mud. In case of large amounts of gas, the pressure could remain of a significant positive value.

In this regard, it can be shown that the gas content R may be determined in accordance with the following equation:

$$R = \frac{K P_2 P_4}{P_2 - P_4} \quad (1)$$

where:
$K$ = a calibration constant
$P_2$ = initial "high" pressure of mud ingested into chamber D $P_4$ = final "reduced" pressure of fluid (mud and gas) in chamber D after piston 32 has completed its upward stroke The pressure $P_2$ and $P_4$ are of course sensed by transducer 21, and converted into appropriate and corresponding electrical signals which may be read at the surface. One such transducer is described in co-pending application of George E. Lewis entitled, "Fluid Pressure Transducer".

The mud connection 19 to pipe 13 may be equipped with a screen (indicated at 60) to restrain the entrance of large well cuttings into the sampling chamber. To ensure that the screen is clean at all times, the effective area of chamber B is made greater than half the effective area of chamber C, causing the up stroke of plunger 20 to be slower than the down stroke. This will clean the screen of lodged, large particles, during each stroke cycle.

The hydraulic operating system is interconnected in such manner as to use a minimum of hydraulic fluid. The pressure supply as at bottle 42 is connected to chambers A and B and to the 3-way control valve 41, so that during the upward stroking, fluid flows into chambers A and B while chamber C is exhausted. When chamber C is connected to pressure supply 42, plunger 20 will be caused to travel downwardly. The fluid in A and B will then rejoin the pressure supply fluid, and will be used in filling a large portion of the requirement to fill chamber C. Only the difference between the volumes of C and the sum of A and B will be furnished from the supply line. Thus, we see that only the fluid volume of C (displaced in one direction) is required for each complete up-down cycle.

The 3-waye solenoid valve 41 may be electrically energized to the up travel position and spring returned to the down travel position of the plunger 20. In the up travel condition, chamber C is typically vented to the ocean (in off-shore application) and the pressure is blocked. In the down travel condition, chamber C is connected to pressure and the vent is blocked.

An automatic adjustable timing circuit, such as shown in FIG. 2, is used to control the cycling of the mud sampling unit. It will also connect the pressure transducer to a signal conditioning unit 65 once each cycle to measure the initial mud pressure $P_2$ and the expanded gas pressure $P_4$. These pressures will indicate the presence of gas in the mud. The higher the pressure $P_4$, the greater the amount of gas in the mud. If this gas pressure is compared with the initial mud pressure $P_2$, as by a suitable signal conditioner 65, a direct reading indication of the amount of gas in the mud can be determined. Further correction can be made to improve the accuracy of the reading if needed by introducing a temperature factor. The temperature variation of the mud in the sampler will vary only a small amount due to the consistency of the sea water temperature at the ocean bottom location of the sampler.

The signal from the transducer is put through the signal conditioner 65, the output from which is used to operate an alarm indicating a gas content of a set level in the mud and to drive a recorder 66 showing the value of the gas content of the mud.

Referring now to FIG. 2, the transducer is shown as incorporating bonded strain gages 51 and 52 which are strained in proportion to the fluid pressure sensed by the transducer. Other gage resistors 151 and 152 are connected with resistors 51 and 52 in a bridge circuit 53, as shown, and wires 57 and 58 in a sub-sea cable 56 connect the bridge with surface signal conditioner 65. Wire 60 in cable 56 supplies current from positive bus 62 to the bridge, as shown, return current passing via wire 61 to negative bus 63. Signal conditioner 65 receives the bridge output and performs the analog calculation indicated by equation (1), and the resultant R value (gas content of the mud) is displayed by a recorder 66. An alarm 67 may be employed to indicate a danagerous gas content in the mud, which could lead to a well blowout.

The solenoid driver 70 for valve 41 may also be supplied with current via wire 60, when relay coil 71a is energized in response to closing of push button 72 at the surface.

We claim:

1. In a drilling mud gas content detector, the combination comprising
  a. a housing defining a mud sample chamber, and having a first bore and a port communicable with well piping containing pressurized mud,
  b. a first plunger movable in the first bore in one direction to return a mud sample in the chamber out said port to said piping, and movable in the opposite direction in the first bore to ingest a pressurized mud sample into said chamber via said port, and
  c. valve means controlling said port and responsive to plunger movement in said opposite direction to block flow of mud to the sample chamber prior to subsequent completion of said plunger movement in said opposite direction which effects a predetermined volume increase producing a reduction of pressure exerted by the sample in the chamber, said pressure reduction being indicative of the mud gas content,
  d. whereby the fluid pressure of the sample in the chamber may be sensed by a sensor in communication with said chamber both prior to and subsequent to said pressure reduction,
  e. said valve means including a second plunger movable in a second bore defined by said housing in response to first plunger movement, said first plunger disengaging the second plunger upon closing of said port and prior to said completion of opposite direction movement of the first plunger,
  f. the first plunger having a primary piston surface to receive fluid pressure application in a third bore defined by the housing and tending to urge the first plunger in said opposite direction.

2. The combination of claim 1 wherein the valve means includes an annular seat engageable by the second plunger, the second plunger having a piston section to receive fluid pressure application tending to urge the second plunger in said opposite direction for valve closing engagement with the seat.

3. In a drilling mud gas content detector, the combination comprising
  a. a housing defining a mud sample chamber, and having a first bore and a port communicable with well piping containing pressurized mud,
  b. a first plunger movable in the first bore in one direction to return a mud sample in the chamber out said port to said piping, and movable in the opposite direction in the first bore to ingest a pressurized mud sample into said chamber via said port,
  c. valve means controlling said port and responsive to plunger movement in said opposite direction to block flow of mud to the sample chamber prior to subsequent completion of said plunger movement in said opposite direction which effects a predetermined volume increase producing a reduction of pressure exerted by the sample in the chamber, said pressure reduction being indicative of the mud gas content,
  d. whereby the fluid pressure of the sample in the chamber may be sensed by a sensor in communication with said chamber both prior to and subsequent to said pressure reduction,
  e. said valve means including a second plunger movable in a second bore defined by said housing in response to first plunger movement, said first plunger disengaging the second plunger upon closing of said port and prior to said completion of opposite direction movement of the first plunger, the valve means including an annular seat engageable by the second plunger, the second plunger having a piston section to receive fluid pressure application tending to urge the second plunger in said opposite direction for valve closing engagement with the seat, and
  f. a source of working fluid pressure communicating with the housing for application to said piston section.

4. The combination of claim 3 wherein the first plunger has a primary piston surface to receive fluid pressure aplication in a third bore defined by the housing and tending to urge the first plunger in said opposite direction.

5. The combination of claim 1 wherein the first plunger has a secondary piston surface to receive fluid pressure application tending to urge the first plunger in said one direction.

6. The combination of claim 5 wherein the housing contains a primary port to communicate said fluid pressure to said primary piston surface, and a secondary port to communicate said fluid pressure to said secondary piston surface.

7. The combination of claim 6 including a source of fluid pressure in communication with said primary port and a control valve movable between a first position in which said source is in communication with said secondary piston surface via said valve and secondary port, and a second position in which pressure fluid in communication with the secondary piston surface is exhausted via the secondary port and valve.

8. The combination of claim 1 including said well piping extending vertically, said housing being vertically elongated and extending proximate said piping, with said first plunger located above said second plunger.

9. The combination of claim 1 including said sensor in communication with said sample chamber.

10. In a drilling mud gas content detector, the combination comprising
   a. a housing defining a mud sample chamber, and having a first bore and a port communicable with well piping containing pressurized mud,
   b. a first plunger movable in the first bore in one direction to return a mud sample in the chamber out said port to said piping, and movable in the opposite direction in the first bore to ingest a pressurized mud sample into said chamber via said port, and
   c. valve means controlling said port and responsive to plunger movement in said opposite direction to block flow of mud to the sample chamber prior to subsequent completion of said plunger movement in said opposite direction which effects a predetermined volume increase producing a reduction of pressure exerted by the sample in the chamber, said pressure reduction being indicative of the mud gas content,
   d. whereby the fluid pressure of the sample in the chamber may be sensed by a sensor in communication with said chamber both prior to and subsequent to said pressure reduction,
   e. said valve means including a second plunger movable in a second bore defined by said housing in response to first plunger movement, said first plunger disengaging the second plunger upon closing of said port and prior to said completion of opposite direction movement of the first plunger, the valve means including an annular seat engageable by the second plunger, the second plunger having a piston section to receive fluid pressure application tending to urge the second plunger in said opposite direction for valve closing engagement with the seat, the area of the first bore exceeding the area of the second bore.

11. The combination of claim 10 wherein the area of the third bore exceeds the area of the first bore.

12. The combination of claim 11 including a sampling piston on the first plunger and movable in the first bore.

13. In apparatus of the character described coupled to an undersea riser pipe in which drilling mud under pressure is circulating upwardly,
   a. means to extract a sample of the drilling mud from the riser at an undersea location,
   b. means to reduce the pressure of the sample at a location outside the riser pipe by subjecting said sample to a predetermined volume increase and
   c. means to sense the pressure of the sample before and after said pressure reduction,
   d. said first mentioned means including ducting outside and communicating with the interior of the riser pipe for returning the bulk of the same to the riser pipe interior following said pressure reduction.

14. In the method of determining the gas content of well drilling mud under pressure within a well pipe, the steps that include
   a. extracting pressurized mud from the well pipe, to thereby provide a first sample,
   b. reducing the pressure of the first sample, by subjecting said sample to a predetermined volume increase
   c. sensing the fluid pressure of the first sample prior to and following said pressure reduction,
   d. returning most of the first sample to the well pipe while retaining a portion of the first sample outside the well pipe,
   e. again extracting pressurize mud from the well pipe and combining same with said retained portion of the first sample to thereby provide a second sample,
   f. reducing the pressure of the second sample by subjecting said sample to a predetermined volume increase and
   g. sensing the fluid pressure of the second sample prior to and following said pressure reduction thereof.

* * * * *